US00PP33992P2

(12) United States Plant Patent
Graff

(10) Patent No.: US PP33,992 P2
(45) Date of Patent: Mar. 1, 2022

(54) ***LAVANDULA* PLANT NAMED 'QL1'**

(50) Latin Name: ***Lavandula stoechas* ssp. *pedunculata***
Varietal Denomination: QL1

(71) Applicant: Plantinova SL, Cabrils (ES)

(72) Inventor: Poul Graff, Sabro (DK)

(73) Assignee: Plantinova SL

( * ) Notice: Subject to any disclaimer, the term of this patent is extended or adjusted under 35 U.S.C. 154(b) by 0 days.

(21) Appl. No.: 17/315,683

(22) Filed: May 10, 2021

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Lavandula* cultivar named 'QL1' is disclosed, characterized by dense, upright plants abundantly producing inflorescences with violet infertile bracts and darker violet true flowers. The new variety is a *Lavandula*, normally produced as an outdoor garden or container plant.

2 Drawing Sheets

Latin name of the genus and species: *Lavandula stoechas* ssp. *pedunculata.*

Variety denomination: 'QL1'.

BACKGROUND OF THE INVENTION

A product of a planned breeding program conducted by the inventor, Sabro Denmark. The objective of the breeding program was to produce new Lavender varieties for ornamental commercial applications. The open pollination resulting in this new variety was made during 2017.

A breeding block of more than 50 different unpatented, unnamed proprietary *Lavandula stoechas* ssp. *pedunculata* was organized for cross pollination, with the resulting seed bulk collected. The new variety was selected in July of 2019 by the inventor in a group of seedlings resulting from this cross-pollination. Exact parents cannot be identified.

Asexual reproduction of the new cultivar was performed by vegetative terminal cuttings. This was first performed at a research greenhouse in Denmark during July of 2019 and has shown that the unique features of this cultivar are stable and reproduced true to type in at least 2 successive generations.

SUMMARY OF THE INVENTION

The cultivar 'QL1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'QL1' These characteristics in combination distinguish 'QL1' as a new and distinct *Lavandula* cultivar:

1. Dense, upright plant.
2. Violet infertile bracts, dark violet fertile flowers.
3. Abundant flowering.

The parents cannot be identified for comparison.

COMMERCIAL COMPARISON

Plants of the new cultivar 'QL1' are comparable to the variety *Lavandula* 'LMAPU31-0', U.S. Plant Pat. No. 29,658. The two *Lavandula* varieties are similar in most horticultural characteristics; however, the new variety 'QL1' differs in producing plants which are more upright, with longer internodes and longer flowerheads.

Plants of the new cultivar 'QL1' are comparable to the variety *Lavandula* 'Larkman Bee', U.S. Plant Pat. No. 20,840. The two *Lavandula* varieties are similar in most horticultural characteristics; however, the new variety 'QL1' differs in producing longer infertile bracts. Additionally plants of 'QL1' are more upright than this comparator.

Plants of the new cultivar 'QL1' can also be compared to the commercial variety *Lavandula* 'Larkman Hazel' U.S. Plant Pat. No. 20,894. These varieties are similar in most horticultural characteristics however, the new variety 'QL1' differs in producing longer overall inflorescence, of a darker color. Additionally plants of 'QL1' are more upright than the comparator and produce more inflorescences per plant.

BRIEF DESCRIPTION OF THE PHOTOGRAPHS

Figure 1:
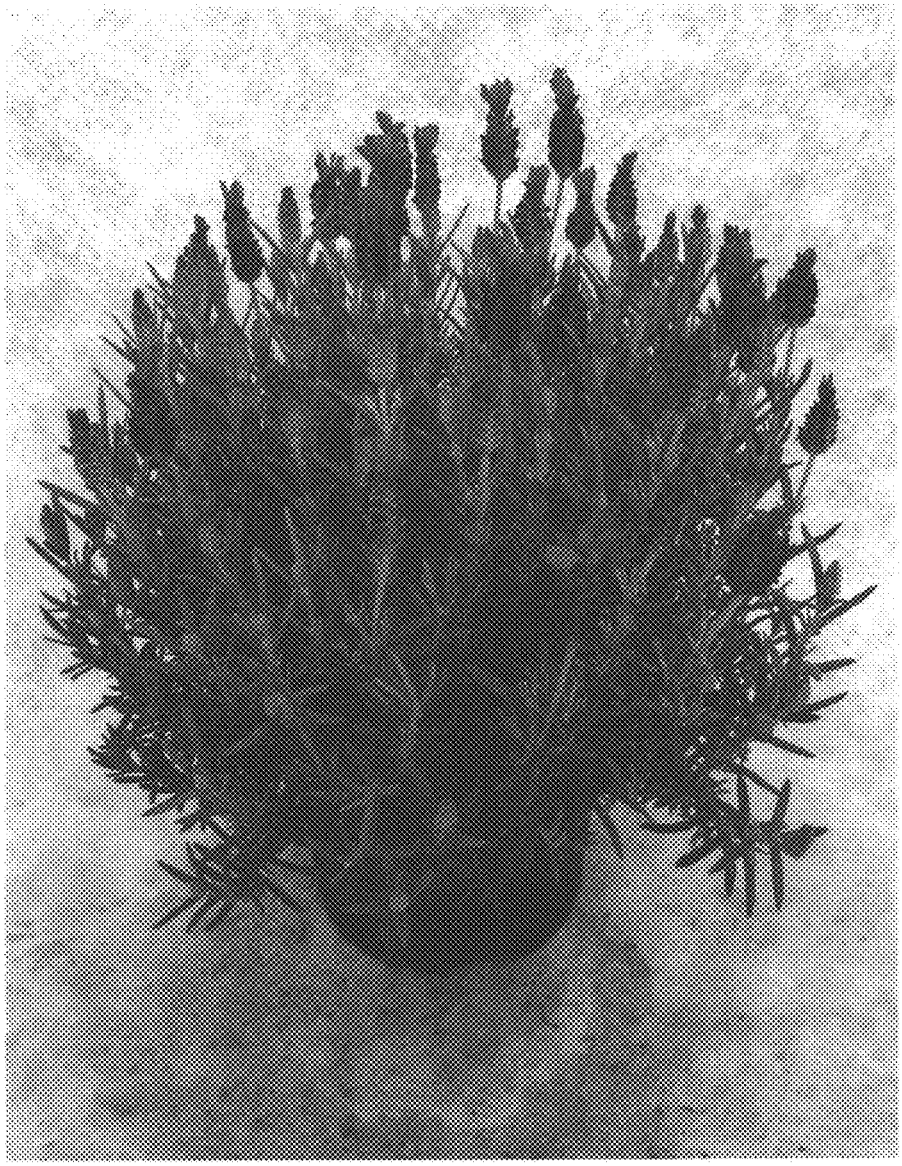
Figure 2:
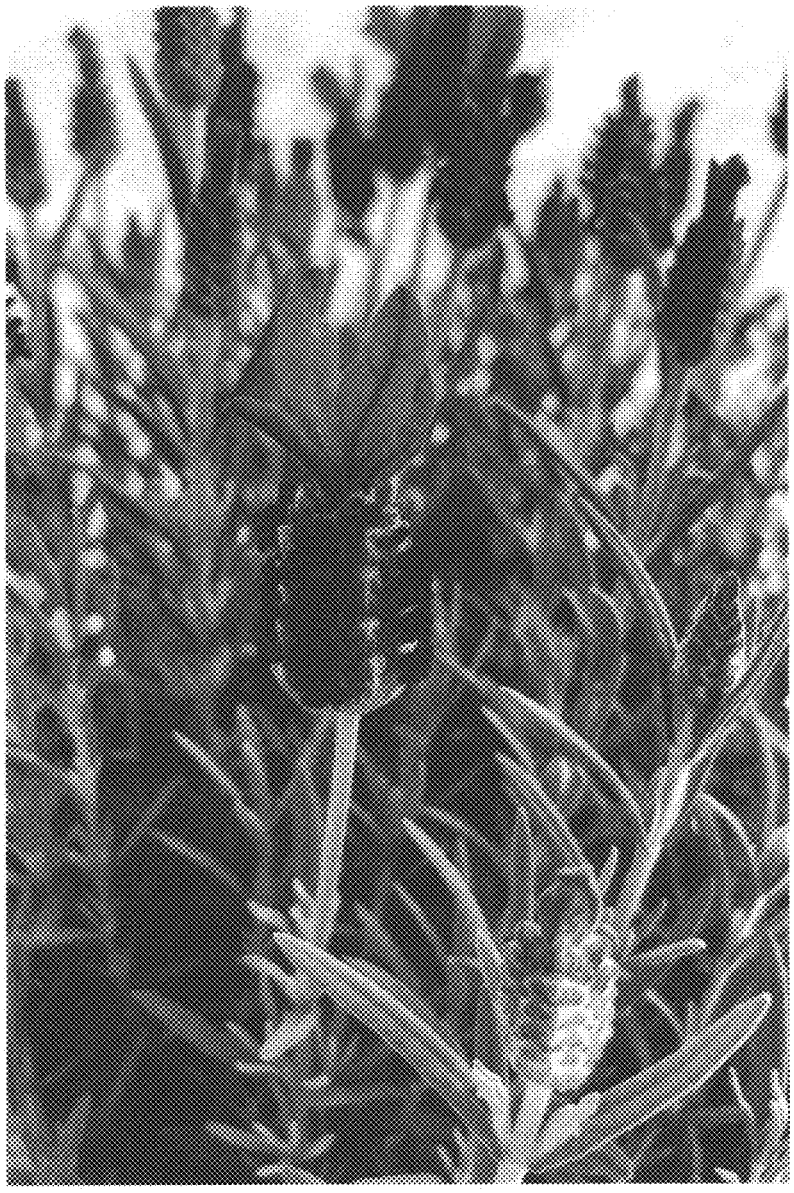

The accompanying photographs in FIG. 1 illustrates in full color a typical plant of 'QL1' grown in a greenhouse in Denmark. Age of the plant photographed is approximately 30 weeks from a rooted cutting. FIG. 2 is a close-up view of the inflorescence.

The photographs were taken using conventional techniques and although colors may appear different from actual colors due to light reflectance are as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QL1' plants grown outdoors during Spring in Denmark. The growing temperature ranged from 10° C. to 35° C. during the day and from 5° C. to 25° C. during the night. General light conditions are bright, normal sunlight. Measurements and numerical values represent averages of typical plant types.

Botanical classification: *Lavandula stoechas* ssp. *pedunculata* 'QL1'.

PROPAGATION

Time to initiate roots: About 10 to 14 days at approximately 21° C.

Time to produce a rooted cutting: About 25 to 35 days at 21° C.

Root description: Well-branched woody main roots expending into fine, fibrous secondary roots. Older roots colored near grey-Brown N199B. Younger roots colored near Grey-Brown 199D and White 155A.

PLANT

Age of plant described: Approximately 9 months from an unrooted cutting.

Plant spread: Approximately 25 cm.

Plant height: Approximately 25 cm.

Plant shape: Rounded and upright, overall forming and upright oval.

Growth rate: Moderate.

Length of primary lateral branches: Approximately 12 to 15 cm.

Diameter of lateral branches: Approximately 3 to 4 mm.

Quantity of lateral branches: About 33 to 45.

Lateral branch color: Near RHS Greyed-Green 194A.

Plant habit: Dense, upright flowering perennial.

Stem:

*Juvenile color.*—Near Green 138C.

*Mature color.*—Near Greyed-Green 191A.

*Texture.*—Puberulent.

Internode length: Average 2.0 cm.

FOLIAGE

Leaf:

*Arrangement.*—2 large opposite leaves at each node.

*Leaf type.*—Simple.

*Quantity.*—Average 36 per main branch.

*Average length.*—Average 2.5 cm.

*Average width.*—Average 3 mm to 4 mm.

*Shape of blade.*—Lanceolate.

*Apex.*—Acute.

*Base.*—Truncate.

*Attachment.*—Sessile.

*Margin.*—Entire.

*Texture of all surfaces.*—Puberbulent.

*Leaf fragrance.*—Typical Lavender scent.

*Color.*—Young foliage upper side: Near RHS Green 138C. Young foliage under side: Near Green RHS 138C. Mature foliage upper side: Near RHS Green 137B. Mature foliage under side: Near Green 138B.

*Venation.*—Type: Reticulate. Venation color upper side: Indistinguishable from foliage color. Venation color under side: Indistinguishable from foliage color.

*Petiole.*—Absent.

FLOWER

Bloom period: Main flush during Spring. Lesser quantities of flowers produced throughout Summer and Fall. During peak flowering total inflorescence quantity 50 per plant.

Inflorescence:

*Form.*—Small single flower in verticillasters arranged in spikes. 6 to 8 rows of flowers, each row typically having 6 to 8 flowers. Flowers have small bracts, and large showy terminal bracts. Number of individual flowers per spike: Average 40 to 50. Inflorescences per plant: Typical range between 40 to 60 during peak flowering. Fragrance: Very strong lavender scent. Inflorescence Size, excluding terminal bracts: Length: Approximately 5 cm. Width: Approximately 2 cm. Shape: Cylindrical. Individual flower: Corolla shape: Salverform. Depth: About 4 mm. Diameter: About 5 mm. Throat Diameter: About 2 mm. Texture: Glabrous all surfaces. Tube Length: 4 mm. Tube Diameter: 2 mm. Tube Texture: Glabrous all surfaces. Tube Color: Exterior near Violet-Blue N92D. Interior near Violet-Blue 93D. Flower Lastingness: About 4 weeks. Petals: Petal Number: 5. Petals Fused or Unfused: Fused at base. Petal Shape: Top 2 lobes obovate, lower 3 lobes ovate. Petal Margin: Entire. Petal Surfaces: Glabrous. Length: Approximately 3 mm. Diameter: Approximately 4 mm at widest opening of petals. Petal Coloration. Immature: Near Purple N79A, upper and lower surfaces. Mature: Near Purple N79A, upper and lower surfaces. Fading: Near Violet 83A, upper and lower surfaces. Calyx: Calyx Width: 3 mm. Calyx Length: 4 mm. Calyx Shape: Flattened tube. Calyx color: RHS Greyed-Purple N187B, flushed N186B. Basal Floral Bracts: Quantity: 1 per individual flower. Bract shape: Broad deltoid. Bract apex: Acute. Margin: Entire. Base: Broadly tapered. Texture: Softly and densely pubescent lower surfaces. Upper surface moderately pubescent. Lastingness: Bracts non-desiccated for approximately 6 weeks. Bract Color: Lower Surface: Greyed-Purple N187B, flushed N186B. Upper Surface: Greyed-Purple N187B, flushed N186B.

Terminal bracts (sterile):

*Quantity.*—4 to 6 per inflorescence.

Large bracts:

*Attitude and angle of attachment.*—Bracts arising at either completely upright, or at a 15 degree angle from the top of the inflorescence.

*Length.*—Approximately 2.2 cm.

*Width.*—Approximately 9 mm.

*Form.*—Petaloid.

*Margin.*—Entire and very slightly undulating.

*Surface.*—Smooth.

*Appearance.*—Matte.

*Shape.*—Oblanceolate.

*Apex.*—Acute.

*Base.*—Attenuate.

*Vein pattern.*—Reticulate.

*Duration on plant.*—Approximately 12 weeks, with good color. Persistent.

*Color.*—Upper side of immature bract: Near RHS Violet 86B, veins 86A. Under side of immature bract:

Near RHS Violet 86B, veins 86A. Upper side of mature bract: Near RHS Violet 86C, veins 86A. Under side of mature bract: Near RHS Violet 86C, veins 86A.

Bud:

*Length.*—Approximately 0.6 cm.

*Diameter.*—Approximately 0.4 cm.

*Shape.*—Ovate.

*Color.*—Near RHS Near Violet-Blue N92B.

*Rate of opening.*—Varies with climactic conditions; Approximately 1 week from colored bud to open flower.

Peduncle:

*Peduncle length.*—Average 4 cm.

*Peduncle diameter.*—Approximately 3 mm.

*Aspect.*—Straight.

*Color.*—Near RHS Green 138C.

*Texture.*—Softly and densely pubescent.

REPRODUCTIVE ORGANS

Androecium: Extremely reduced, frequently not present.

*Stamens.*—4.

*Anther shape.*—linear.

*Anther length.*—Approximately 0.5 mm.

*Anther color.*—Near RHS Violet 84D.

*Pollen quantity.*—Pollen production not observed.

Pistil:

*Number.*—1.

*Length.*—Approximately 3 mm.

*Style.*—Length: Approximately 0.2 cm. Color: Near RHS Violet 84D.

*Stigma.*—Shape: Globular. Color: Near RHS Violet 86A. Ovary: Minute and immeasurable.

OTHER CHARACTERISTICS

Seeds and fruits: Seed production not observed to date.

Disease/pest resistance: Neither resistance nor susceptibility to the normal diseases and pests of *Lavandula stoechas* has been observed.

Drought tolerance and cold tolerance: Hardy perennial. Tolerates high temperature to at least 32° C. Tolerates low temperatures to −5° C. While specific drought tolerance has not been observed, once plants are established very little water is necessary to maintain plants.

What is claimed is:

1. A new and distinct cultivar of *Lavandula* plant named 'QL1' as herein illustrated and described.

* * * * *